United States Patent [19]

Chabardes

[11] 4,105,697

[45] Aug. 8, 1978

[54] PROCESS FOR THE PREPARATION OF α, β-ETHYLENIC ALDEHYDES

[75] Inventor: Pierre Chabardes, Sainte-Foy les Lyon, France

[73] Assignee: Rhone-Poulenc Industries, Paris, France

[21] Appl. No.: 702,850

[22] Filed: Jul. 6, 1976

[30] Foreign Application Priority Data

Jul. 18, 1975 [FR] France ................................. 75 22558

[51] Int. Cl.² ........................ C07C 47/20; C07C 45/00
[52] U.S. Cl. .............................................. 260/601 R
[58] Field of Search ....................... 260/601 R, 603 R

[56] References Cited

FOREIGN PATENT DOCUMENTS 1,233,221 5/1971 United Kingdom ................ 260/601 R
1,233,222 5/1971 United Kingdom ................ 260/601 R

OTHER PUBLICATIONS

Larson et al. "J. Org. Chem." vol. 38, No. 22, 1973, pp. 3935–3936.

Primary Examiner—James O. Thomas, Jr.
Assistant Examiner—Werren B. Lone

[57] ABSTRACT

A process for the preparation of α,β-ethylenic aldehydes containing at least 7 carbon atoms by reacting an allyl alcohol with a dienoxytriorganosilane.

16 Claims, No Drawings

PROCESS FOR THE PREPARATION OF α,β-ETHYLENIC ALDEHYDES

BACKGROUND OF THE INVENTION

The present invention relates to a process for the preparation of α,β-ethylenic aldehydes which contain at least 7 carbon atoms, by reaction of a compound containing a 1,3-dienoxy group with an allyl alcohol. More specifically, the present invention relates to a process for obtaining α,β-unsaturated aldehydes having a terpene structure.

German application No. 1,768,552 has proposed the preparation of α,β-ethylenic aldehydes containing at least 7 carbon atoms, and more particularly, of α,β-ethylenic aldehydes containing at least one unit of the general formula:

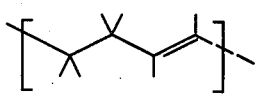
(A)

by reaction of allyl alcohols of various structures with dienyl ethers of the general formula:

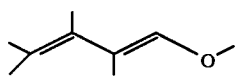
(B)

or their precursors, derived from an enolisable α,β-ethylenic aldehyde or β,γ-ethylenic aldehyde, by heating in the presence of various catalysts. This process constitutes an elegant means of arriving, in particular, at terpene aldehydes such as citral, farnesal or α-sinensal. These aldehydes, as well as the majority of their homologues, are of great industrial interest as intermediates in organic synthesis (citral can be used as an intermediate for the synthesis of vitamin A or of perfumes such as citronellal or hydroxycitronellal) and/or as perfumes or as additives in the foodstuff industry.

In spite of its value, the process described in said German application No. 1,768,552 is not free from disadvantages. Among these, the most objectionable is the difficulty of obtaining the dienyl ethers used as starting compounds. These ethers are generally prepared by passing acetals of α,β-ethylenic aldehydes or β,γ-ethylenic aldehydes, or β-alkoxyacetals of saturated aldehydes, over catalysts at a high temperature (250° to 350° C.); the synthesis of these acetals is also delicate. Thus, the 1-alkoxy-3-methyl-butadienes (1-methoxy- or 1-ethoxy-isoprenes) can be obtained by passing the dimethyl-acetal or diethyl-acetal of β-methylcrotonaldehyde, or 1,1,3-triethoxy- or 1,1,3-trimethoxy-3-methylbutane over a catalyst based on acid magnesium phosphate deposited on sodium silicate. In turn, the 1,1,3-trialkoxy-methyl-butanes are obtained by reaction of an alkyl vinyl ether with acetone acetals, which can be obtained either by acetalisation of acetone or by reaction of a lower alcohol with a vinyl ether [compare I. N. NAZAROV et al., J. Gen. Chem. USSR 29, 116–123 (1959); I. N. NAZAROV et al. Doklad, Akad, Nauk. U.S.S.R., 117, 823–5 (1957)].

In addition to the disadvantages associated with the accessibility of the dienyl ether starting materials, the implementation of the process described in the above-mentioned German application necessitates the use of catalysts which favor the condensation reaction, such as inorganic or organic proton acids, or their salts, or Lewis acids. Furthermore, it appears that this process is only applicable with difficulty in a case where the dienyl ether does not contain a hydrocarbon substituent (for example, a methyl radical) on the carbon atom located in the β-position relative to the ether group; in that case, an α,β-ethylenic aldehyde, resulting from the attachment of the allyl radical to the carbon in the β-position relative to the ether group, is mainly formed [cf. A. F. Thomas, J. Am. Chem. Soc. 91, 3281–3289 (1969)]. According to this author, the presence of a hydrogen atom on the carbon atom in the β-position relative to the ether group would block the reaction at an intermediate stage. The ultimate effect is that the process described in said German application No. 1,768,552 lends itself poorly to the preparation of α,β-ethylenic aldehydes which contain a methyl group in the β-position relative to the aldehyde group but are unsubstituted in the α-position, such as citral and farnesal.

It is, therefore, an object of the present invention to provide a process for preparing α,β-ethylenic aldehydes containing at least 7 carbon atoms without the requirement of a catalyst.

It is also an object of the present invention to provide a process for preparing α,β-ethylenic aldehydes containing at least 7 carbon atoms by condensation of readily available compounds having a system of conjugated double bonds with an allyl alcohol.

Other objects will be apparent to those skilled in the art from the present description.

GENERAL DESCRIPTION OF THE INVENTION

There has now been found, and it is this which constitutes the subject of the present invention, a process for the preparation of α,β-ethylenic aldehydes containing at least 7 carbon atoms, which may or may not be substituted by a hydrocarbon group in the α-position relative to the aldehyde group, by condensation of a compound containing a system of conjugated double bonds with an allyl alcohol, which does not necessitate the use of a catalyst.

More specifically, and preferentially, the present invention relates to a process for the preparation of α,β-ethylenic aldehydes of the general formula (I):

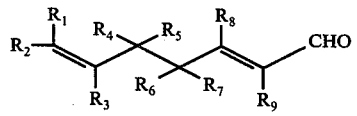
(I)

in which $R_1$, $R_2$, $R_3$, $R_4$, $R_5$, $R_6$, $R_7$, $R_8$ and $R_9$ represent hydrogen atoms or identical or different organic radicals defined below, by reaction, at elevated temperatures, of an allyl alcohol of the general formula (II):

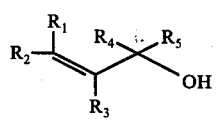
(II)

with a diene compound containing a system of conjugated double bonds, wherein the diene compound is a dienoxytriorganosilane of the general formula (III):

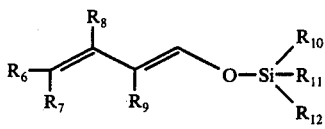 (III)

in which $R_6$, $R_7$, $R_8$ and $R_9$ have the general meaning given above and $R_{10}$, $R_{11}$ and $R_{12}$ represent identical or different organic groups as defined below.

In the present description, the term "lower alkyl radicals" will be applied to linear or branched alkyl radicals containing from 1 to 4 carbon atoms, such as methyl, ethyl, n-propyl, isopropyl, n-butyl, isobutyl, and t-butyl radicals. The term "lower alkenyl radicals" will be applied to alkenyl radicals containing from 2 to 4 carbon atoms, such as the vinyl, prop-1-enyl, allyl, isopropenyl, but-3-enyl, but-2-enyl, but-1-enyl, 1-methyl-prop-2-enyl, methallyl and isobutenyl radicals.

More specifically, the various radicals shown in the formulae (I) and (III) have the following meaning:

$R_1$, $R_2$ and $R_4$, which may be identical or different represent (a) linear or branched alkyl radicals containing from 1 to 25 carbon atoms and optionally substituted by monocyclic, dicyclic or tricyclic cycloalkyl or cycloalkenyl radicals which contain from 5 to 8 carbon atoms per ring and which can carry 1 to 3 lower alkyl or alkenyl radicals, or optionally substituted by heterocyclic radicals with 5 or 6 chain members containing a hetero-atom taken from the group of oxygen and sulphur, and also containing one or two ethylenic double bonds;

(b) linear or branched alkenyl radicals containing from 2 to 30 carbon atoms and from 1 to 12 conjugated or non-conjugated ethylenic double bonds optionally substituted by cycloalkyl, cycloalkenyl or heterocyclic radicals such as those defined under "(a)";

(c) cycloalkyl or cycloalkenyl radicals containing from 5 to 8 carbon atoms and, where appropriate, 1 or 2 ethylenic double bonds, and optionally substituted by 1 to 3 lower alkyl or alkenyl radicals;

(d) aryl radicals containing 1 or 2 fused or non-fused benzene nuclei and optionally substituted by 1 to 3 lower alkyl radicals;

(e) arylalkyl radicals containing 1 or 2 carbon atoms in the alkyl radical and 1 or 2 benzene nuclei in the aryl radical; and (f) heterocyclic radicals with 5 chain members, containing a hetero-atom taken from the group of sulphur and oxygen and optionally containing 1 or 2 ethylenic double bonds, and where appropriate, substituted by 1 or 2 lower alkyl radicals.

$R_3$ and $R_5$, which can be identical or different, symbolize (a) linear or branched alkyl or alkenyl radicals having from 1 to 8 carbon atoms;

(b) cycloalkyl or cycloalkenyl radicals containing 5 or 6 carbon atoms and optionally substituted by 1 to 3 lower alkyl radicals;

(c) aryl radicals containing 1 or 2 fused or non-fused benzene nuclei and optionally substituted by 1 to 3 lower alkyl radicals; and (d) arylalkyl radicals such as those defined above for $R_1$, $R_2$ and $R_4$.

$R_1$ or $R_2$ can also form, with $R_3$ or $R_4$ or $R_5$, and carbon atoms to which these various radicals are linked, an aliphatic ring or a system of 2 or 3 aliphatic rings containing 1 or 2 ethylenic double bonds and from 5 to 10 carbon atoms, and optionally substituted by 1 to 4 lower alkyl or alkenyl radicals, so that two of the above-mentioned radicals $R_1$ or $R_2$ and $R_3$ or $R_4$ or $R_5$ together form an alkylene or alkenylene radical containing from 2 to 8 carbon atoms and optionally substituted by 1 to 4 lower alkyl or alkenyl radicals, or form a divalent radical consisting of an aliphatic hydrocarbon ring containing 4 or 5 carbon atoms or a chain of two methylene groups separated by an aliphatic ring containing 4 carbon atoms.

$R_1$ or $R_2$ can form with $R_3$, and the carbon atoms to which they are linked, a heterocyclic ring with 5 chain members, containing 1 or 2 double bonds, with the aid of a hetero-atom taken from the group of oxygen and sulphur (so that the radicals $R_1$ or $R_2$ form, with the radical $R_3$, a divalent radical containing a terminal hetero-atom).

$R_3$ can form, with $R_4$ or $R_5$ and the carbon atoms to which they are linked, an aliphatic hydrocarbon ring with 6 carbon atoms which optionally contains an ethylenic double bond, where necessary substituted by 1 to 3 lower alkyl radicals.

$R_4$ and $R_5$ can form, with one another and with the carbon atom to which they are linked, an aliphatic hydrocarbon ring such as that previously defined for $R_3$ and $R_4$ or $R_5$.

$R_6$ represents a lower alkyl radical.

$R_7$ represents a linear or branched alkyl radical containing from 1 to 20 carbon atoms, optionally substituted by a cyclohexyl, cyclohexenyl or cyclohexadienyl radical containing, where necessary, from 1 to 3 lower alkyl radicals; a linear or branched alkenyl radical containing from 2 to 20 carbon atoms and 1 to 10 conjugated or non-conjugated ethylenic double bonds, optionally substituted by a cyclohexyl, cyclohexenyl or cyclohexadienyl radical containing, where necessary, 1 to 3 lower alkyl radicals; a cyclohexyl radical containing, where necessary, from 1 to 3 lower alkyl radicals; a cyclohexenyl or cyclohexadienyl radical optionally containing from 1 to 3 lower alkyl radicals; or a phenyl radical optionally substituted by 1 to 3 lower alkyl radicals.

$R_8$ and $R_9$ represent lower alkyl radicals or cyclohexyl or phenyl radicals optionally substituted by 1 to 3 lower alkyl radicals.

$R_{10}$, $R_{11}$ and $R_{12}$ represent alkyl radicals containing from 1 to 10 carbon atoms; cycloalkyl radicals containing from 5 to 8 carbon atoms; aryl radicals containing 1 or 2 benzene nuclei, optionally substituted by 1 or 2 lower alkyl radicals; and arylalkyl radicals; two at most of $R_{10}$, $R_{11}$ and $R_{12}$ radicals can represent, moreover, a group of the formula (IV):

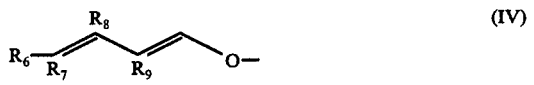 (IV)

By way of specific examples of the radicals $R_1$, $R_2$ and $R_4$, there may be mentioned alkyl radicals, such as the methyl, ethyl, propyl, n-butyl, isobutyl, t-butyl, pentyl, 4-methyl-pentyl, n-hexyl, n-heptyl, 3-methyl-hexyl, n-octyl, n-nonyl, 4-methyl-octyl, 1,4-dimethyl-pentyl, n-decyl, 4,8-dimethyl-nonyl, n-undecyl, n-dodecyl, n-pentadecyl, 4,8,10-trimethyl-undecyl, (2',6',6'-trimethyl-cyclohex-1'-enyl)-methyl, 2-(2',6',6'-trimethyl-cyclohex-1'-enyl)-ethyl, 2-(3'-methyl-2'-methylenebicyclo[2.2.1]-hept-3′-yl)-ethyl, 2-(2′,3′-dimethyl-tricyclo-[2.2.1.0]-hept-3′-yl)-ethyl, 6-(2′,2′,6′-trimethyl-cyclohexyl)-4-methyl-hexyl, 6-(2′,6′,6′-trimethyl-cyclohex-1-enyl)-4-methyl-hexyl, and 10-(2′,2′,6′-trimethyl-cyclohexyl)-3,7-dimethyl-decyl radicals; alkenyl radicals, such as the vinyl, allyl, prop-1-enyl, isopropenyl, but-3-enyl, but-2-enyl, but-1-enyl, 1-methyl-prop-2-enyl, methallyl, isobutenyl, buta-1,3-dienyl, 2-methyl-buta-1,3-dienyl, 3-methylbuta-1,3-dienyl, 4-methyl-pent-3-enyl, hex-3-enyl, hexa-3,5-dienyl, 5-methyl-hexa-3,5-dienyl, 2,4-dimethyl-pent-3-enyl, 3,4-dimethyl-pent-3-enyl, 1,4-dimethyl-pent-3-enyl, 2,4-dimethylpenta-2,4-dienyl, 2,3,4-trimethyl-penta-2,4-dienyl, 4,8-dimethylnona-3,7-dienyl, 4,8-dimethyl-nona-3,8-dienyl, 2-(2′,6′,6′-trimethyl-cyclohex-1′-enyl)-vinyl, 3-(2′,6′,6′-trimethyl-cyclohexa-1′,3′-dienyl)-1-methyl-prop-1-enyl, 5-(2′,6′,6′-trimethyl-cyclohexa-1′,3′-dienyl)-3-methyl-penta-1,3-dienyl, 6-(2′,6′,6′-trimethyl-cyclohexa-1′,3′-dienyl)-4-methyl-hexa-1,3,5-trienyl and 6-(2′,6′,6′-trimethyl-cyclohex-1′-enyl)-4-methyl-hexa-1,3,5-trienyl radicals; cycloalkyl radicals, such as cyclohexyl, 2-methyl-cyclohexyl, 2,6,6-trimethyl-cyclohexyl and cycloheptyl radicals; cycloalkenyl radicals, such as the cyclohex-1-enyl, 2-methyl-cyclohex-1-enyl, 2,6,6-trimethyl-cyclohex-1-enyl, and 2,6,6-trimethyl-cyclohexa-1,3-dienyl radicals; aryl radicals such as phenyl, toluyl, or α- or β-naphthyl radicals; aryl-alkyl radicals, such as the benzyl radical; and the furanyl-1 and thienyl-1 radicals.

As illustrative examples of radicals R₃ and R₅, there may, in particular, be mentioned alkyl radicals, such as methyl, n-propyl, isopropyl and n-hexyl radicals; alkenyl radicals, such as vinyl, the propenyl radicals, the butenyl radicals and the pentenyl radicals, the cyclohexyl radicals, the cyclohexenyl radicals, and the phenyl, α-naphthyl and benzyl radicals.

Among the divalent radicals formed together by R₁ or R₂ with R₃ or R₄ or R₅, there may, in particular, be mentioned the trimethylene, tetramethylene and 2-methyl-propylene radicals and the radicals of the formulae:

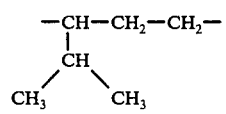 (C)

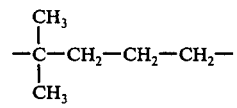 (D)

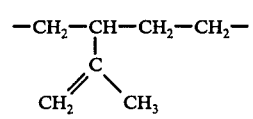 (E)

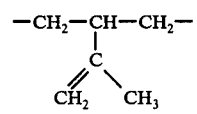 (F)

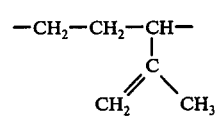 (G)

-continued

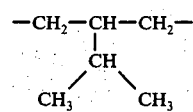 H

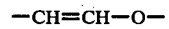 (I)

 (J)

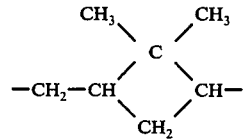 (K)

Among the divalent radicals which R₃ can form with R₄ or R₅, or which the latter can form with one another, there may be mentioned the tetramethylene radical or the radical of the formula (D).

As examples of radicals R₆, there may be mentioned the methyl and ethyl radicals; R₇ can be a methyl, ethyl, propyl, isopropyl, n-hexyl, n-decyl, n-pentadecyl, vinyl, buta-2,3-dienyl, 3-methyl-buta-1,3-dienyl, cyclohexylmethyl, β-cyclohexylethyl, β-(2′,6′,6′-trimethyl-cyclohex-1′-enyl)-ethyl and 3,7,11-trimethyl-dodeca-1,3,6,10-tetraenyl radicals; R₈ and R₉ can be alkyl radicals, such as methyl, ethyl and propyl radicals; and, by way of examples, R₁₀, R₁₁ and R₁₂ can be methyl, ethyl, propyl, butyl, cyclohexyl, phenyl, toluyl or benzyl radicals.

In the formulae (I) to (IV), inclusive, the symbols R₁ to R₁₂ preferably represent the following:

R₁, R₃, R₄ and R₅: hydrogen or a lower alkyl radical.

R₂: a hydrogen atom, a linear or branched alkyl radical containing from 1 to 10 carbon atoms and more particularly a lower alkyl radical optionally substituted by a furanyl or cyclohexyl or cyclohexenyl radical containing from 1 to 3 methyl substituents, an alkenyl radical as defined above under "(b)", a cycloalkyl or cycloalkenyl radical optionally substituted by 1 to 3 methyl groups and containing 5 or 6 carbon atoms, an aryl radical or an arylalkyl radical; alternatively, R₂ preferably forms, with R₃, a tetramethylene radical or one of the radicals (C), (E), (I), (J) and (K).

R₆, R₇, R₈ and R₉: a hydrogen atom or a lower alkyl radical.

R₁₀, R₁₁ and R₁₂: a lower alkyl radical or a phenyl or cyclohexyl radical.

More preferentially still:

R₁ and R₃ represents a hydrogen atom or a methyl or ethyl group;

R₄ and R₅ represent a hydrogen atom;

R₂ represents a methyl, ethyl, furanylmethyl, thenylmethyl, phenyl, benzyl, 2,6,6-trimethyl-cyclohex-1-enyl, (2,6,6-trimethyl-cyclohex-1-enyl)-methyl, 2-(2′,6′,6′-trimethyl-cyclohex-1′-enyl)-ethyl, 2-(2′,6′,6′-trimethyl-cyclohex-1′-enyl)-vinyl, or 2-(2′,6′,6′-trimethyl-cyclohex-1′-enyl)-2-methyl-vinyl radical, or an alkenyl radical of the general formula (V):

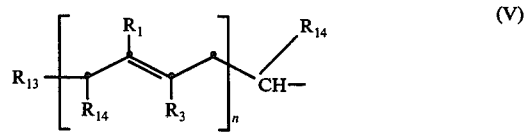 (V)

in which $R_1$, $R_3$ and $R_{14}$ represent a hydrogen atom or a methyl or ethyl radical, $R_{13}$ represents a hydrogen atom or a furanylmethyl, thenylmethyl, phenyl or 2,6,6-trimethyl-cyclohex-1-enyl radical, $n$ is an integer ranging from 1 to 5 and preferably is 1 or 2, and the $n$ units of the general formula:

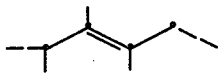

can be identical or different.

As examples of allyl alcohols of the formula (II), there may be mentioned, without implying a limitation: allyl alcohol, crotyl alcohol, methallyl alcohol, prenol (3-methyl-but-2-en-1ol), 3-methyl-pent-2 en-1-ol, penta-2,4-dien-1-ol, pent-2-en-1-ol, pent-1-en-3-ol, dimethylvinyl-carbinol, 2-methyl-but-1-en-3-ol, 2-methyl-but-2-en-1-ol (tyglyl alcohol), hex-2-en-1-ol, 3-methyl-hex-2-en-1-ol, hexa-2,4-dien-1-ol, cyclohex 2-en-1-ol, 2,3-dimethyl-but-2-en-1-ol, 3-methyl-hexa-2,4-dien-1-ol, 4-methyl-pent-3-en-2-ol, 4-methyl-hex-3-en-2-ol, hept-2-en-1-ol, 1-hydroxymethyl-cyclopentene, 3,4-dimethyl-pent-2-en-1-ol, hexa-1,3-dien-5-ol, hepta-2,6-dien-1-ol, 5-methyl-hexa-2,4-dien-1-ol, 2-methyl-hexa-3,5-dien-2-ol, hept-1-en-3-ol, 5-methyl-hex-1-en-3-ol, 5-methyl-hex-2-en-4-ol, methyl-n-propyl-vinyl-carbinol, methyl-ethyl-isopropenylcarbinol, 5-methyl-cyclohex-2-en-1-ol, 1-hydroxymethyl-cyclohexene, oct-2-en-1-ol, oct-2-en-4-ol, 6-methyl-hept-1-en-3-ol, 6-methyl-hept-2-en-4-ol, octa-2,6-dien-1-ol, 1-vinyl-cyclohexanol, 2-methyl-1-hydroxymethyl-cyclohexene, cyclohex-1-en-2-yl-ethanol, octa-1,7-dien-3-ol, non-2-en-1-ol, 7-methyl-non-2-en-1-ol, 5-methyl-oct-5-en-4-ol, di-n-propyl-vinylcarbinol, 7-methyl-octa-2,,6-dien-1-ol, 7-methyl-octa-1,7-dien-3-ol, nona-2,6-dien-1-ol, cinnamyl alcohol, α-phenylallyl alcohol, α-cyclo-hexylallyl alcohol, dec-2-en-1-ol, dec-1-en-3-ol, geraniol, nerol, β-cyclogeraniol, linalol, 2,7-dimethyl-octa-1,6-dien-3-ol, 2,7-dimethyl-oct-1-en-3-ol, 3,7-dimethyl-oct-1-en-3-ol, perillyl alcohol, carveol, p-menthadienol, carvotanacetol, 4-phenyl-but-3-en-2-ol, 4-phenyl-crotyl alcohol, 1-n-octyl-allyl alcohol, 4-methyl-dec-1-en-3-ol, piperitol, o-, m- or p-methyl-cinnamyl alcohol, α-benzylallyl alcohol, 4-cyclohexyl-crotyl alcohol, 4-(cyclohex-1'-enyl)-crotyl alcohol, α-naphthyl-allyl alcohol, 3,7,11-trimethyl-dodec-1-en-3-ol, 5-phenyl-penta-2,4-dien-1-ol, 3,7,11-trimethyl-dodec-2-en-1-ol, farnesol, nerolidol, retinol, phytol, 3,4-dehydro-retinol, isophytol, β-ionylidene-ethanol, 4-(β-naphthyl)-crotyl alcohol, furfuryl alcohol, myrtenol, thenyl alcohol and 9-(furyl-3')-3,7-dimethyl-nona-2,6-dienol.

Among the allyl allohols mentioned above, it is preferred to use the primary alcohols ($R_4$ and $R_5$ represent hydrogen in the formula (II)) and more particularly still, the allyl alcohols corresponding to the general formula (VI):

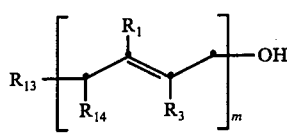

where $R_1$, $R_3$, $R_{13}$ and $R_{14}$ have the meaning givenl for the formula (V), $m$ is an integer ranging from 1 to 6, and preferably 1 to 3, and the $m$ units of the formula:

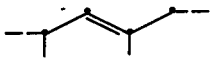

can be identical or different.

The dienoxytriorganosilanes of the formula (III), which are employed for carrying out the process of the invention, are known products which are easily prepared, for example, by reaction of a triorganohalogenosilane (in particular, the triorganochlorosilanes) with an enolisable α,β- or β,γ-ethylenic aldehyde in the presence of zinc chloride, in accordance with the process described in Belgian Pat. No. 670,769. The following may be mentioned by way of non-limiting examples of the dienoxytriorganosilanes of the formula (III): (buta-1,3-dienyloxy)-trimethylsilane, (buta-1,3-dienyloxy)-triethylsilane, (buta-1,3-dienyloxy)-dimethyl-ethylsilane, (buta-1,3-dienyloxy)-triphenylsilane, (buta-1,3-dienyloxy)-dimethylphenylsilane, (3-methyl-buta-1,3-dienyloxy)-trimethylsilane, (2-methyl-buta-1,3-dienyloxy)-trimethylsilane, (hexa-1,3-dienyloxy)-trimethyl-silane, (4-methyl-penta-1,3-dienyloxy)-trimethylsilane, (3-methyl-penta-1,3-dienyloxy)-trimethylsilane, (2-methyl-hexa-1,3-dienyloxy)-trimethylsilane, (3,4-dimethyl-penta-1,3-dienyloxy)-triethylsilane, (4-cyclohexyl-buta-1,3-dienyloxy)-triethyl-silane, (3,7-dimethyl-octa-1,3,6-trienyloxy)-triethylsilane, (3,7,11-trimethyl-dodeca-1,3,6,10-tetraenyloxy)-trimethylsilane and (4-[2,',6',6'-trimethyl-cyclohex-1'-enyl]-3-methyl-hexa-1,3-dienyloxy)-trimethylsilane.

Among the α, β-ethylenic aldehydes which can be prepared by the process according to the invention, there may be mentioned especially: hepta-2,6-dien-1-al, 2-methyl-hepta-2,6-dienal, 3-methyl-hepta-2,6-dienal, 3,6-dimethyl-hepta-2,6-dienal, citral, octa-2,6-dienal, 2-methyl-octa-2,6-dienal, farnesal, sinensal, 7,11-dimethyl-dodeca-2,6,10-trienal, 3,7-dimethyl-9-(2',6',6'-trimethyl-cyclohex-1'-enyl)-nona-2,4,6-trienal, 3,5,7-trimethyl-octa-2,6-dienal, 3-methyl-7phenyl-hepta-2,6-dienal, 2,7-dimethyl-octa-2,6-dienal, 2,6-dimethyl-octa-2,6-dienal, 2,7,11-trimethyl-dodeca-2,6,10-trienal, 2,6,10-trimethyl-dodeca-2,6,10-trienal, 3,6,11-trimethyl-dodeca-2,6,10-trienal, 2-methyl-5-(furyl-2')-pent-2-enal, 2-methyl-4-(thenyl-2')-but-2-enal, 9-(fural-3')-2,6-dimethyl-nona-2,6-dienal, 2-methyl-4-(α-pineyl-8')-but-2-enal, 2-methyl-4-(1'-methyl-4'-isopropenyl-cyclohex-1'-en-6'-yl)-but-2-enal, 3,7,11,15-tetramethyl-hexadeca-2,6,10,14-tetraenal, 5-(2',6',6'-trimethyl-cyclohex-1'-enyl)-3-methyl-pent-2-enal, 3-ethyl-7-methyl-octa-2,6-dienal and 3,7,11,15,19-pentamethyl-eiscosa-2,6-dienal. These aldehydes are useful in perfumery and scent compositions and as flavoring materials.

The process according to the invention is very particularly suitable for the preparation of aldehydes of the general formula (VII):

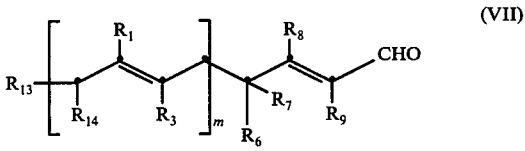

in which $R_1$, $R_3$, $R_{13}$, $R_{14}$ and $m$ have the meaning given for the formula (VI) and $R_6$, $R_7$, $R_8$ and $R_9$ each represent hydrogen or a lower alkyl radical, and espcially those in which $R_{14}$, $R_6$ and $R_7$ each represent a hydrogen atom and $R_8$ and $R_9$ represent a methyl or ethyl radical.

This process constitutes a convenient means of increasing the skeleton of an aldehyde of the formula (III) from 1 to $m$ units of the formula:

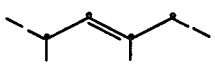

For this, it suffices to reduce the $\alpha,\beta$-ethylenic aldehyde obtained at any stage, by the usual means, to the corresponding alcohol and to use the latter as the allyl alcohol starting material for a new condensation.

Without intending to limit the scope of the invention to a particular reaction mechanism, the condensation of the allyl alcohols of the formula (II) with the aldehydes of the formula (III) can be illustrated by the following equation:

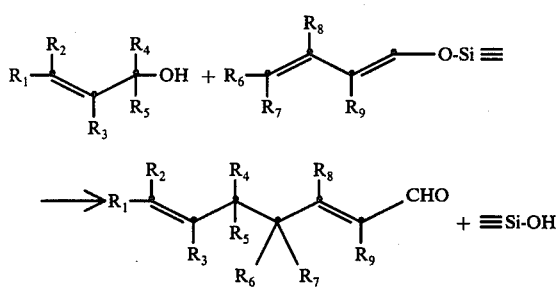

It has, in fact, been found that during the reaction a triorganosilanol forms, which can be completely or partially in the form of a hexaorganodisiloxane. Such a reaction course appears unexpected because those skilled in the art would have had to expect the liberation of the enolisable ethylenic aldehyde used as starting material for the synthesis of the dienoxy-silane, with formation of the corresponding allyloxysilane. As a matter of fact, according to G. L. Larson et al., J. Org. Chem. 38, 3996 (1973), the reaction of an alcohol with 2-trimethylsilyloxy-propene leads to the formation of acetone and of the alkoxytrimethylsilane corresponding to the alcohol employed.

The hexaorganodisiloxane formed during the condensation is a by-product of industrial value; it is, in fact, used as a chain stopper for the production of polysiloxane polymers. It can also be converted to a triorganochlorosilane by the usual processes (for example, by reaction with thionyl chloride), and the triorganochlorosilane can be used to prepare the dienoxysilane starting material. The triorganosilanol formed can be condensed, in an acid medium, to give the corresponding hexaorganodisiloxane.

The molar ratio of dienoxysilane to allyl alcohol can vary within wide limits because it is possible to employ equimolecular amounts of the two reactants or an excess of one or the other. In general, it is preferred to employ a least 1.2 mols, and more particularly, at least 1.5 mols, of dienoxysilane per mol of allyl alcohol. There is no upper limit to the amount of dienoxysilane and the latter can actually constitute the reaction medium; thus, it is possible to use an excess of 10 to 20 mols of dienoxysilane relative to the stoichiometric amount.

The reaction temperature can be between about 50° and 350° C. and preferably between about 90° and 250° C. If the reactants are volatile under the selected temperature conditions, the reaction can be carried out under the autogenic pressure, or under the pressure of an inert gas such as nitrogen. This pressure can in that case be between 2 and 50 bars.

The reaction can be carried out in the absence of any solvent if the reactants are liquid under the chosen temperature conditions; the excess of one or other of the reactants can then play the role of a solvent; however, the reaction can also be carried out in the presence of a solvent which is inert towards the reactants under the conditions employed. Among the solvents conforming to this requirement there may be mentioned saturated aliphatic hydrocarbons, such as hexane, heptane and octane; saturated cycloaliphatic hydrocarbons, such as cyclopentane and cyclohexane; aromatic hydrocarbons, such as benzene, toluene, xylene and ethylbenzene; halogated hydrocarbons, such as 1,2-dichloroethane, trichloroethane, chlorobenzene and p-dichlorobenzene; ethers, such as 1,2-dimethoxyethane, diglyme and tetrahydrofurane; esters, such as ethyl acetate and methyl benzoate; and nitriles, such as acetonitrile and propionitrile.

The reaction time depends on the chosen conditions, especially on the temperature, and can vary between a few minutes and several hours, for example, from 10 minutes to 20 hours.

The process according to the invention can be carried out continuously or discontinuously. When the reaction has ended, the reaction products are easily isolated by the usual techniques, in particular by distillation and/or by extraction by means of solvents.

SPECIFIC DESCRIPTION OF THE INVENTION

In order to disclose more clearly the nature of the present invention, the following examples illustrating the invention are given. It should be understood, however, that this is done solely by way of example and is intended neither to delineate the scope of the invention nor limit the ambit of the appended claims. In the examples which follow, and throughout the specification, the quantities of material are expressed in terms of parts by weight, unless otherwise specified.

EXAMPLE 1

18.7 g. of 1-trimethylsilyloxy-3-methyl-1,3-butadiene and 2.58 g. of prenol are introduced into a 125 cm.³ stainless steel autoclave. The autoclave is closed and argon is introduced until the pressure of 10 bars is reached at 20° C. The contents of the autoclave are then heated to 180° C. for four hours, while stirring. Thereafter, the reaction mixture is cooled to 20° C., the apparatus pressure is released, and its contents are distilled first under normal pressure to remove the fractions of low boiling point, and then under reduced pressure. A fraction in which 2.5 g. of citral were determined by gas-liquid chromatography, the citral being identified by infrared spectrography, is thus isolated.

The yield amounts to 53.3% relative to the prenol introduced.

EXAMPLE 2

The procedure of Example 1 is followed, but with a molar ratio of dienoxysilane/prenol of 2 instead of 4, and in the presence of 15 cm.³ of hexane. 3.25 g. of a fraction distilling between 60° and 65° C. under 0.5 mm. of mercury, in which 61% of citral were determined, corresponding to a yield of 43% relative to the prenol introduced are thus obtained.

As will be appreciated by those skilled in the art, by repeating the foregoing examples, replacing the 1-trimethylsilyloxy-3-methyl-1,3-butadiene with other dienoxysilanes in accordance with the foregoing disclosure and teachings, compounds in accordance with the invention can be produced. Similarly, by replacing the prenol with other allyl alcohols in accordance with the foregoing disclosures and teachings, other compounds in accordance with the invention can be produced.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed.

What is claimed is:

1. A process for the preparation of α,β-ethylenic aldehydes of the general formula:

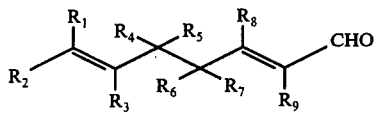   (I)

in which
$R_1$, $R_2$ and $R_4$ represent a member of the group consisting of hydrogen, and:
(a) alkyl radicals containing from 1 to 25 carbon atoms; and
(b) alkenyl radicals containing from 2 to 30 carbon atoms; and
$R_3$ and $R_5$ are members of the group consisting of hydrogen and alkyl or alkenyl radicals having from 1 to 8 carbon atoms;
$R_6$ is a member of the group consisting of hydrogen and a lower alkyl radical;
$R_7$ is a member of the group consisting of hydrogen and an alkyl radical containing from 1 to 20 carbon atoms; an alkenyl radical containing from 2 to 20 carbon atoms, and
$R_8$ and $R_9$ are members of the class consisting of hydrogen and lower alkyl radicals, by reacting, at elevated temperatures of between about 50° and 350° C., an allyl alcohol of the general formula:

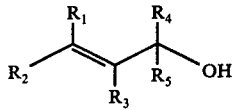   (II)

in which $R_1$ to $R_5$ have the meaning given above, with a dienoxy compound containing two conjugated ethylenic double bonds, wherein said dienoxy compound is a dienoxy triorganosilane of the general formula:

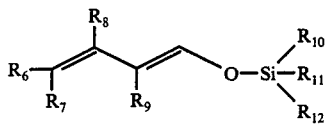   (III)

in which $R_{10}$, $R_{11}$ and $R_{12}$, represent alkyl radicals containing from 1 to 10 carbon atoms, cycloalkyl radicals containing from 5 to 8 carbon atoms, two at most of $R_{10}$, $R_{11}$ and $R_{12}$ radicals representing a group of the formula:

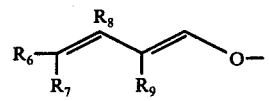

and $R_6$ to $R_9$ have the meaning given for the formula (I).

2. A process according to claim 1, wherein the molar ratio of dienoxytriorganosilane compound to allyl alcohol is from at least 1 to 10.

3. A process according to claim 1, wherein the molar ratio of dienoxytriorganosilane compound to allyl alcohol is from at least 1.2.

4. A process according to claim 1, wherein the process is carried out at superatmospheric pressure.

5. A process according to claim 1, wherein the process is carried out in the presence of a solvent which is inert under the reaction conditions.

6. A process according to claim 5, wherein the solvent is of the group consisting of saturated aliphatic hydrocarbons, saturated cycloaliphatic hydrocarbons, aromatic hydrocarbons and their halogenated derivatives, ethers, esters and nitriles.

7. A process according to claim 1, wherein in the alcohol of formula (I), $R_1$, $R_3$, $R_4$ and $R_5$ represent hydrogen or a lower alkyl radical.

8. A process according to claim 1, wherein $R_1$, $R_3$, $R_4$ and $R_5$ represent a hydrogen atom or a methyl or ethyl radical.

9. A process according to claim 1, wherein $R_2$ represents a member of the group consisting of a hydrogen atom and an alkyl radical containing from 1 to 10 carbon atoms.

10. A process according to claim 1, wherein in the allyl alcohol of the general formula (II):
$R_1$ and $R_3$ each represent a member of the class consisting of a hydrogen atom, a methyl group, and an ethyl group,
$R_4$ and $R_5$ represent a hydrogen atom,
$R_2$ represents a member of the class consisting of methyl and ethyl.

11. A process according to claim 1, wherein the allyl alcohol used is a member of the class consisting of allyl alcohol, crotyl alcohol, methallyl alcohol, and prenol.

12. A process according to claim 1, wherein in the dienoxytriorganosilane of the formula (III):
$R_6$, $R_7$, $R_8$ and $R_9$ each represent a member of the class consisting of a hydrogen atom and a lower alkyl radical, and
$R_{10}$, $R_{11}$ and $R_{12}$ each represent a member of the class consisting of a lower alkyl radical.

13. A process according to claim 1, wherein the dienoxytriorganosilane is a member of the group consisting of (buta-1,3-dienyloxy)-trimethylsilane, (2-methyl-buta-1,3-dienyloxy)-trimethylsilane, (3-methyl-buta-1,3-dienyloxy)-trimethylsilane, and (3-methyl-penta-1,3-dienyloxy)-trimethylsilane.

14. A process according to claim 1, wherein the aldehyde produced is of the general formula:

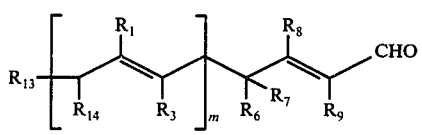 (VII)

in which $R_1$, $R_3$, $R_{13}$ and $R_{14}$ are each a member selected from the class consisting of hydrogen, a methyl radical and an ethyl radical, $m$ represents an integer from 1 to 6, and $R_6$, $R_7$, $R_8$ and $R_9$ each represent hydrogen or a lower alkyl radical, are prepared by reaction of an allyl alcohol of the general formula:

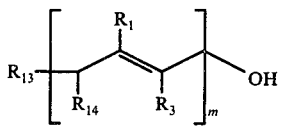 (VI)

in which $R_1$, $R_3$, $R_{13}$ and $R_{14}$ and $m$ have the meaning given above, with a dienoxysilane of the formula (III), in which $R_6$ to $R_9$ each represent hydrogen or a lower alkyl radical, at between 50° and 350° C., the $m$ units of the structure:

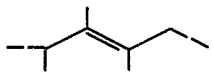

in the formulae (VI) and (VII).

15. A process according to claim 14, wherein $m$ is an integer from 1 to 3.

16. A process according to claim 14, wherein citral and farnesol are prepared by reaction of prenol and geraniol or nerol with (3-methyl-buta-1,3-dienyloxy)-trimethylsilane.

* * * * *